(12) United States Patent
Goode et al.

(10) Patent No.: US 9,101,449 B2
(45) Date of Patent: Aug. 11, 2015

(54) FILTER REMOVAL DEVICE

(75) Inventors: Louis B. Goode, Cranberry Township, PA (US); Chun Kee Lui, Apollo, PA (US); Robert Booker, Vandegrift, PA (US); Michael W. Emmert, Apollo, PA (US); Charles L. McIntosh, Silver Springs, MD (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/610,963

(22) Filed: Sep. 12, 2012

(65) Prior Publication Data

US 2014/0031854 A1 Jan. 30, 2014

Related U.S. Application Data

(60) Provisional application No. 61/676,603, filed on Jul. 27, 2012.

(51) Int. Cl.
*A61F 2/01* (2006.01)

(52) U.S. Cl.
CPC ............. *A61F 2/01* (2013.01); *A61F 2002/011* (2013.01)

(58) Field of Classification Search
CPC ................ A61F 2/01; A61F 2002/011; A61B 2010/0208; A61B 17/3207
USPC ........... 606/159, 167, 170, 200; 600/566, 567
See application file for complete search history.

(56) References Cited

U.S. PATENT DOCUMENTS

| | | | |
|---|---|---|---|
| 5,135,531 A * | 8/1992 | Shiber ........................ | 606/159 |
| 5,836,968 A | 11/1998 | Simon et al. | |
| 5,928,260 A | 7/1999 | Chin et al. | |
| 5,928,261 A | 7/1999 | Ruiz | |
| 6,007,558 A | 12/1999 | Ravenscroft | |
| 6,156,055 A | 12/2000 | Ravenscroft | |
| 6,258,026 B1 | 7/2001 | Ravenscroft et al. | |
| 6,342,062 B1 | 1/2002 | Snon et al. | |
| 6,344,048 B1 | 2/2002 | Chin et al. | |
| 7,041,117 B2 | 5/2006 | Snon et al. | |
| 7,279,000 B2 | 10/2007 | Cartier et al. | |
| 7,314,477 B1 | 1/2008 | Ravenscroft et al. | |
| 7,534,251 B2 | 5/2009 | WasDyke | |
| 7,544,202 B2 | 6/2009 | Cartier et al. | |
| 7,678,119 B2 | 3/2010 | Little et al. | |
| 7,749,244 B2 | 7/2010 | Brucheimer et al. | |

(Continued)

OTHER PUBLICATIONS

Cable. (n.d.). Dictionary.com *Unabridged*. Retrieved Oct. 10, 2014, from Dictionary.com website: http://dictionary.reference.com/browse/cable.*

*Primary Examiner* — Thomas McEvoy
(74) *Attorney, Agent, or Firm* — Woodard, Emhardt, Moriarty, McNett & Henry LLP

(57) ABSTRACT

There are disclosed embodiments of a system for retrieving a filter device from within a patient. A tube or sheath and one or more cables or other elongated members, which include a protrusion such as a bead at or adjacent a distal end, are movable with respect to each other. When the tube or sheath is adjacent a filter device, the cable or elongated member is extended so that the protrusion is between or through wires of the filter, and the protrusion is engaged to or between two or more of the wires. The filter is placed within the tube or sheath, as by retracting the cable or elongated member to pull the filter, by moving the tube or sheath over the cable or elongated member while it engages the filter under tension, or both.

20 Claims, 4 Drawing Sheets

(56) References Cited

U.S. PATENT DOCUMENTS

| | | |
|---|---|---|
| 7,794,473 B2 | 9/2010 | Tessmer et al. |
| 7,846,175 B2 | 12/2010 | Bonnette et al. |
| 7,967,838 B2 | 6/2011 | Chanduszku et al. |
| 8,025,668 B2 | 9/2011 | McCartney |
| 8,109,962 B2 | 2/2012 | Pal |
| 8,118,828 B2 | 2/2012 | Cartier et al. |
| 2008/0033290 A1* | 2/2008 | Saadat et al. ............ 600/433 |
| 2010/0048987 A1 | 2/2010 | Khairkhahan |
| 2011/0022038 A1* | 1/2011 | Seshadri et al. ............ 606/7 |
| 2011/0040321 A1 | 2/2011 | Cartier et al. |

* cited by examiner

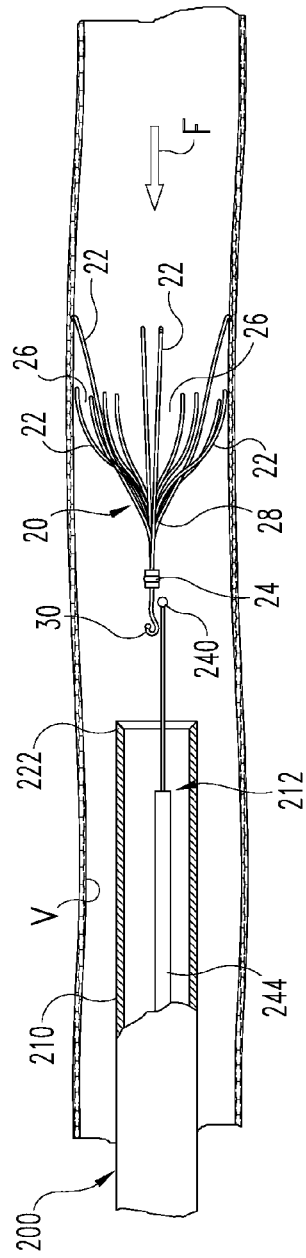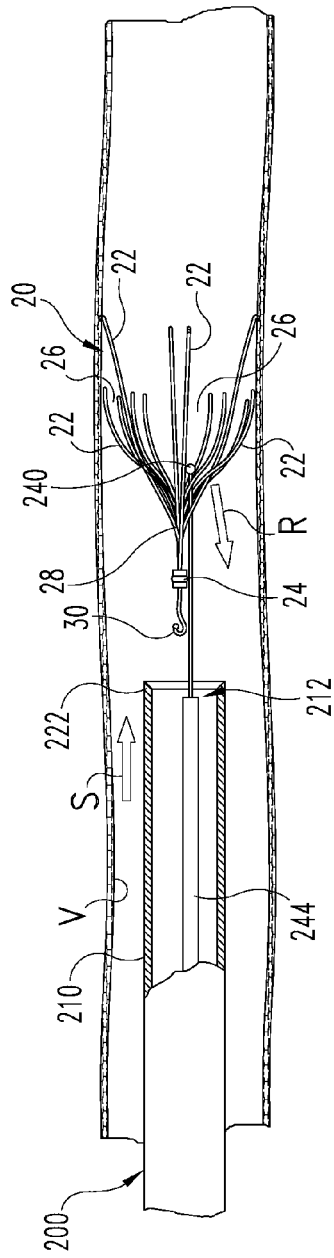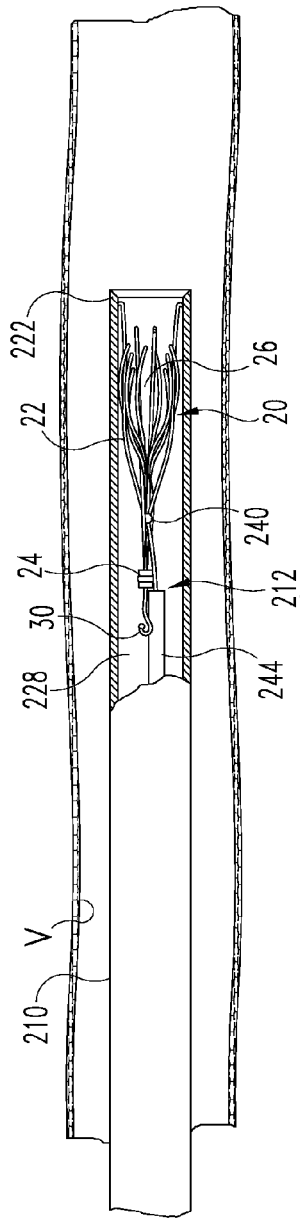

FILTER REMOVAL DEVICE

REFERENCE TO RELATED APPLICATION

This application claims the benefit of U.S. Provisional Patent Application Ser. No. 61/676,603 filed Jul. 27, 2012, which is hereby incorporated by reference.

The present disclosure relates to medical devices. More particularly, the disclosure relates to devices for removing or retrieving filters for clots or other obstructions placed in vessels or other locations in a patient.

BACKGROUND

Filtering devices that are percutaneously placed in blood vessels have been available for many years. A need for filtering devices can arise, for example, in trauma patients, orthopedic surgery patients, neurosurgery patients, or in patients having medical conditions requiring bed rest or non-movement. During such medical conditions, the need for filtering devices arises where there is a likelihood of thrombosis in the peripheral vasculature of patients wherein clot material, stenosis material or other particles break away from the vessel wall, risking downstream blockage of the vessel or other damage. For example, depending on the size, such breakaway material could pose a serious risk of pulmonary embolism, i.e. wherein blood clots migrate from the peripheral vasculature through the heart and into the lungs. A filtering device can be deployed in the vasculature of a patient when, for example, anticoagulant therapy is contraindicated or has failed. In more recent years, filters have been used or considered in preoperative patients and in patients predisposed to thrombosis which places the patient at risk for embolism.

The benefits of a vascular filter have been well established. However, in many cases filters have not been considered removable from a patient due to the likelihood of endotheliosis of the filter or fibrous reaction matter adherent to the endothelium during treatment. Following deployment of a filter in a patient, proliferating intimal cells can begin to accumulate around the filter struts which contact the wall of the vessel. After a length of time, such ingrowth may prevent removal of the filter, or may risk significant trauma during removal through a layer of endothelium, requiring the filter to remain in the patient. Thus, filtering devices may remain implanted in the patient for life, even though the condition or medical problem that required the device has passed, because of difficulty or risk in removal. Where removal has been considered, some filters have been provided with a hook for gripping and pulling (e.g. by intravascular forceps or other catheter-borne device) in order to remove it. Such hooks can be difficult to find or latch onto in vivo, and may be covered by cellular growth.

Accordingly, devices and methods dedicated to easier and more effective removal of intravascular filters are needed.

SUMMARY

Among other things, there are disclosed embodiments of a retriever device or system for an intravascular filter having a plurality of wire portions each separated by at least one gap, which includes a sheath having a lumen and at least one elongated member at least partially within the lumen. The sheath and elongated member are movable longitudinally with respect to each other. The elongated member includes a distal end and a bead or other protrusion (e.g. ball or knot) at or adjacent the distal end, and the sheath includes a tip portion having a distal-facing edge and an inner surface proximal of the edge and narrowing as it extends proximally of the edge. The tip portion can include an outer surface, with the edge separating the outer surface and inner surface. That outer surface in particular embodiments includes a plurality of substantially flat surfaces substantially parallel to a longitudinal axis of the sheath. The inner surface may border a portion of the lumen and narrow as it extends away from the edge, which can be a circular sharp edge. In certain embodiments, the elongated member is a cable, and/or a bead is substantially spherical, having a diameter smaller than a largest width of one of the filter gaps and larger than a smallest width of the one of the filter gaps. Multiple cables or other elongated members are provided in particular embodiments, and may be movable with or independently of each other.

Specific embodiments are disclosed of a retrieval system for retrieving an emplaced internal medical filter that include a retrieval sheath having a body portion that includes a lumen at least in a distal portion, the sheath having a tip portion with a central opening communicating with the lumen, an outer surface and an inner surface, with the outer surface and the inner surface meeting in at least one edge. A cable extends at least partially through the retrieval sheath, the cable having a distal end and a protrusion at or adjacent the distal end. The cable and sheath are movable longitudinally with respect to each other between a first relative position in which the bead extends beyond the tip portion of the retrieval sheath by at least one-quarter of a length of the filter and a second relative position in which the bead is within the retrieval sheath. The cable has a length dimension and the bead has a lateral dimension substantially perpendicular to the length dimension that is wider than at least a portion of a gap in the filter. In certain embodiments, the edge is a circular sharp edge or a rounded blunt edge. The retrieval sheath can have the tip portion centered on the sheath's longitudinal axis, and the outer surface can include at least one substantially flat surface that is substantially parallel to the axis. For example, the outer surface may be essentially or exclusively a plurality of substantially flat surfaces that are substantially parallel to the axis. Particular embodiments of the bead are substantially spherical or substantially linear and non-parallel to a longitudinal axis of the elongated member.

Methods for retrieving or removing an intravascular filter that has been placed within a patient's vessel are also disclosed. Such methods can include inserting a retriever device into the patient to a position adjacent the filter, the retriever including a sheath and an elongated member at least partially within the sheath, the elongated member having a protrusion at or adjacent a distal end. The elongated member is moved longitudinally with respect to the sheath so that the bead engages a portion of the filter. One or both of the elongated member and sheath are moved relative to each other while maintaining the bead and a portion of the filter in engagement, until at least a portion of the filter is within the sheath, and the retriever device is removed from the patient, with the filter at least partially within the sheath. Embodiments of methods can include, during the moving of one or both of the elongated member and sheath, moving a distal-facing edge of the retriever device with respect to the vessel toward the filter, the edge moving between the wall of the vessel and the filter. During the moving of one or both of the elongated member and sheath, the bead can pull the filter along the vessel. Following the moving of one or both of the elongated member and sheath, in particular embodiments all of the filter is within the sheath after the moving.

The disclosed device embodiments for retrieving an emplaced internal medical filter may feature a tubular member having a lumen and a tip portion with a central opening communicating with the lumen, the tip portion having at least one distal-facing edge, and a thin elongated member longitudinally movable through the lumen and having a bead at or adjacent a distal end. The protrusion or bead can be extended beyond the tip portion of the tubular member by an amount sufficient to retrieve a filter and can be retracted to a position within the tubular member. In particular, the cable may be extendable so that the bead can extend through a gap in a filter and engage the filter, and the tubular member and the elongated member are adapted for operation to place the filter and engaged bead within the lumen.

As particular examples, embodiments of a filter removal or retrieval device have one or more protrusions, which may be characterized as beads, balls, and/or knots, on or toward the end of a cable, so that such bead(s), ball(s) and/or knot(s) (and a portion of the cable) can be easily introduced into the heart of the filter. When withdrawn, the protrusion (e.g. bead or ball) becomes captured as the cable is drawn up into one of the V-shapes formed by the filter wires. A sheath through which the cable extends is equipped with a tip capable of freeing an embedded portion of the filter (if any). Once the filter is tethered by the protrusion and cable it allows for pulling the cable to move the filter toward the sheath and/or advancing the sheath while holding the filter in place.

BRIEF DESCRIPTION OF THE DRAWINGS

FIGS. 7-9 are part-cross-sectional views indicating use of filter retrieval systems as disclosed.

DESCRIPTION OF THE ILLUSTRATED EMBODIMENTS

Figure 1:
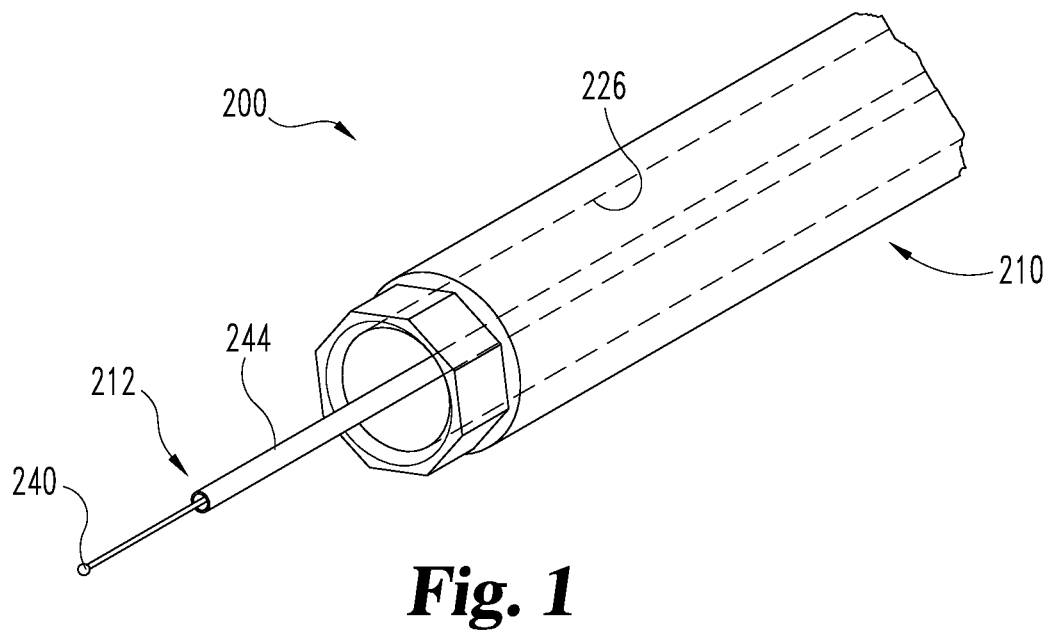
FIG. 1 is a perspective view of an embodiment of an internal filter retrieval system.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated embodiments, and such further applications of the principles of the disclosure as illustrated therein being contemplated as would normally occur to one skilled in the art to which the disclosure relates.

Referring now generally to the drawings, there is shown an exemplary type of filter 20 for use in the circulatory system to contain travel of emboli (e.g. clotted blood, stenosed material or other potential obstructions). As will be discussed further below, in certain embodiments filter 20 is inserted into and at least temporarily emplaced or fixed within a vessel (e.g. vein or artery) so that blood flow (see arrow F in FIG. 7) is directed through it. Emboli carried along by the flow are caught and held by filter 20, so that they do not move into organs or other vasculature and present a danger to the patient. As noted previously, however, removal of filter 20 from its location in the vessel can present difficulties.

In the illustrated embodiment, filter 20 includes a series of wires 22 joined by a collar or crimp 24. Collar 24 generally forms a first end for relative downstream placement within a vessel, so that free ends of wires 22 extend in a direction generally away from collar 24 to a relative upstream location. In an unstressed (e.g. non-compressed) condition, wires 22 form a somewhat outwardly-flared device, with the free ends of wires 22 positioned radially outward and longitudinally displaced from collar 24. Thus, filter 20 has a larger upstream aspect or dimension at those free ends, with wires 22 engaging the inside of a vessel at or near the free ends, and it narrows to collar 24. Gaps 26 between individual wires 22 (not all of which are numbered in the drawings to maintain clarity) allow flow through filter 20, and are relatively wide at or adjacent the free ends, and narrow substantially toward collar 24 (or other meeting or gathering place for wires 22). Gaps 26 at or adjacent to collar 24 narrow to pinch-points 28, which may be substantially V-shaped or similarly configured. Accordingly, emboli, tissue fragments or other material undesirable in the blood stream are caught by the converging portions of wires 22, and can be resorbed into the blood or removed with filter 20. The exemplary filter 20 is also shown with a hook 30, which as noted previously can be used to retrieve or position filter 20, assuming it is accessible.

Filter 20 is generally collapsible toward and expandable from a longitudinal axis A through collar 24. Wires 22 are single strands of thin wire in particular examples, of biocompatible materials such as stainless steel, Nitinol or other superelastic material(s), combinations of such superelastic materials with other compatible materials, or other flexible and sturdy material. Thus, wires 22 can be flexed in toward axis A for enclosure in a catheter or other transport device (not shown) for placement in a vessel, and when moved out of the catheter within the vessel, wires 22 expand to or toward a natural or unstressed condition, against the vessel wall. It is to be understood that filter 20 is one example, and that devices as disclosed herein are usable with other available or contemplated filters.

A system or device 200 for use in removing intravascular filters (e.g. filter 20) from the body generally includes a tubular retrieval sheath 210 and at least one elongated member or cable 212 that extends through sheath 210. Operating together, sheath 210 and cable 212 can be used to remove most or all available filters, without regard to whether the filter has a hook or other particular feature designed for connection to a removal device. System 200 will be generally described with respect to filters within a blood vessel, as a particular example of the types of filters and body locations that may be indicated. However, it will be understood that usage in other contexts or locations and/or with other types of devices may also be indicated.

Sheath 210 is a tubular device having a body portion 220 and a tip portion 222. The illustrated embodiment of body portion 220 has an outer wall surface 224 defining an outer diameter and an inner wall surface 226 defining a lumen 228 with an inner diameter. In particular embodiments, the wall of body portion 220 has a constant thickness throughout, or may have a constant thickness in at least particular locations. Body portion 220 in the illustrated embodiment has a length sufficient to extend through a vessel (by itself or in conjunction with an outer catheter or other conduit) to a filter. For example, body portion 220 may have a length sufficient to extend from outside the patient through a percutaneous entry into the cardiovascular system (introducer or other structure) via one or more vessels to the location of the filter. In such embodiments, for instance, a proximal portion or end of body portion 220, and/or an operating portion attached to it, is outside the body, while a distal portion (including tip 222) is adjacent the filter. Preferably, body portion 220 is of a semi-flexible plastic or other material, such as materials used for intravascular catheters, to allow body portion 220 to move through vessels while maintaining integrity and allowing loading of the filter, as further explained below.

Currently-available sheaths are sized to be small in diameter while still permitting a folded filter to fit within them, as is naturally suggested by placement of such sheaths in the vasculature. In particular embodiments of body portion 220, the outer diameter is larger than currently available sheaths. It is to be noted that the figures are not necessarily to scale, and as an example embodiments of sheath 210 may approach a vessel wall more closely than may be indicated in them. As will be described further below, such a larger outer diameter can assist in removing filters from vessels that have become surrounded or attached to cells or tissue, or perhaps at least partially embedded in or along the endothelium of a vessel. As examples of such a larger outer diameter, body portion 220 can have an outer dimension approximately 11 French, allowing for flow around body portion 220, while enabling the outer dimension to approach the wall of the vessel and move through cells or tissue in which portion(s) of the filter may be embedded.

Figure 2:
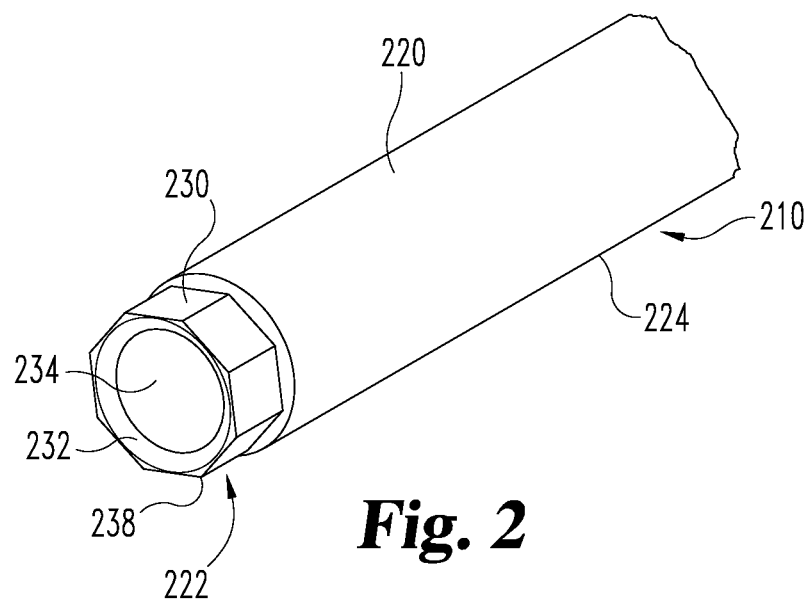
FIG. 2 is a perspective view of an embodiment of a portion of the embodiment of FIG. 1.
Figure 3:
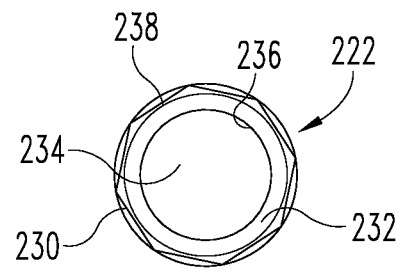
FIG. 3 is an end view of an embodiment of a distal end of the embodiment of FIG. 2.
Figure 4:
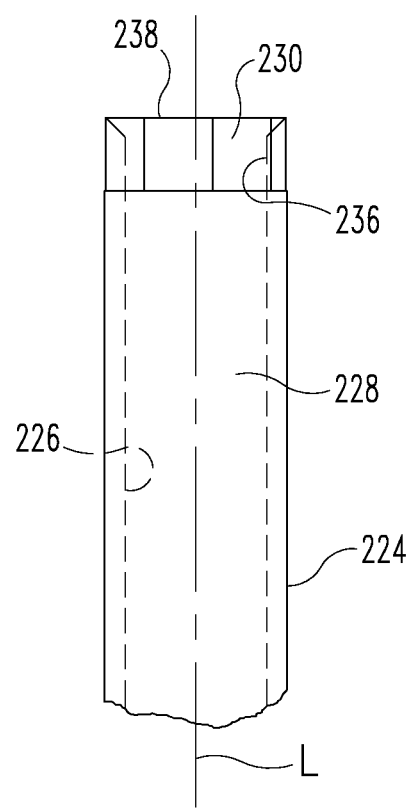
FIG. 4 is a side view of an embodiment of a portion of the embodiment of FIG. 2.
Figure 5:
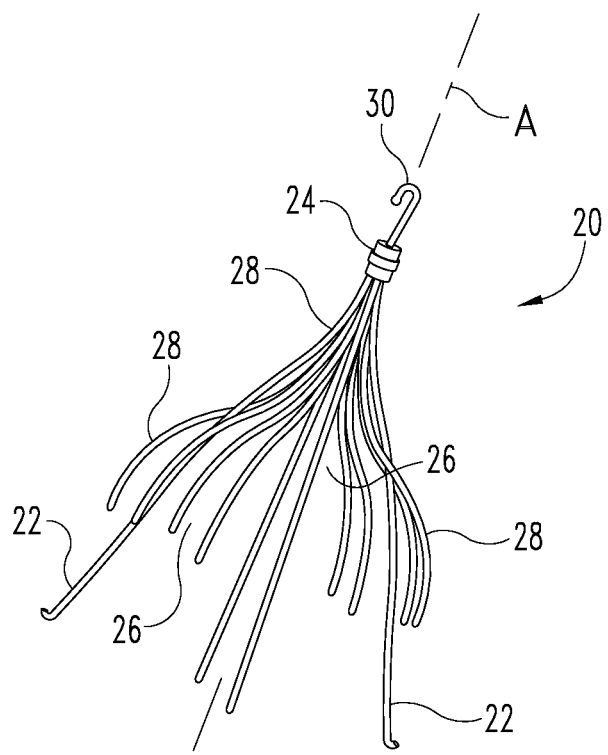
FIG. 5 is a perspective view of a type of internal filter.

Tip 222 is located at a distal end of body portion 220, and is designed for engaging tissue or cells on or around the filter to help free the filter (if necessary) and remove it. Tip 222 is fixed with respect to body portion 220 in the illustrated embodiment, although other embodiments may permit tip 222 to rotate to some degree or otherwise move with respect to body portion 220. As seen in the embodiment of FIGS. 1-3, tip 222 is roughly circular or annular, with an outer surface or set of surfaces 230, an inner surface 232, and an opening 234. In the illustrated embodiment, inner surface 232 and lumen 228 meet at a line or joint 236, but are essentially part of the same aperture, with inner surface 232 widening lumen 228 and/or opening 234 distally.

Outer surface 230 is shown in the illustrated embodiment as a series of regular planar surfaces that are parallel (or substantially so) to a central longitudinal axis L of tip 222. This embodiment of surfaces 230 are or are analogous to an external print for a nut or other mechanical device, and in the illustrated embodiment has 10 separate flats or surfaces. Inner surface 232 slopes inward toward opening 234 from an edge or meeting 238 with surfaces 230. Edge 238 is at least approximately circular or annular in this embodiment, and may be blunt (e.g. rounded as it extends from outer surface 230 to inner surface 232) or sharp (e.g. as a thinned or beveled portion). In the illustrated embodiment, inner surface 232 has a concave aspect, i.e., a slope that increases with respect to axis L as inner surface 232 approaches line or joint 236. Such a shape provides a relatively wide mouth of tip portion 222 with a part that will exert inward pressure on a filter that is being moved into lumen 228 of sheath 210. Similarly, in other embodiments inner surface 232 may have a substantially conical shape, or be slightly convex.

In embodiments in which tip 222 is inserted into body 220, a sleeve or collar (not shown) of tip portion 222 can be inserted into lumen 228 of sheath 210, and the smallest diameter of opening 234 (e.g. at or around line 236) will be at least slightly smaller than the diameter of lumen 228. In embodiments in which tip 222 is attached to a distal end or portion of sheath 210, opening 234 may have a smallest diameter that is the same as or at least slightly larger than that of lumen 228. The illustrated embodiment shows a proximal portion of the tip 222 extending proximally from the proximal end of surfaces 230, and in this embodiment that proximal end or portion of tip 222 is inserted with an interference fit, adhesive, and/or other fixing method into sheath 210.

Cable 212 extends part or all of the way through sheath 210. Cable 212 and sheath 210 are longitudinally movable with respect to each other. For example, cable 212 is extendable and retractable with respect to sheath 210 and tip 222, and/or sheath 210 and tip 222 are movable over cable 212. The term "cable" is intended to refer to any of a variety of semi-rigid substantially linear structures adapted for use as described herein, and may include cables (i.e. woven, wrapped or twisted wires or other filaments), wire(s) or other filament(s) in a non-wrapped condition, thin flexible solid rods, or similar structures.

Cable 212 includes a bead, knot or other type of protrusion 240 having a lateral dimension (e.g. a width perpendicular to the length of cable 212) that is greater than the diameter of the remainder of cable 212, which in the illustrated embodiment forms or is at or adjacent the distal end of cable 212. Bead 240 is in the shape of a ball or sphere in this embodiment, and in other embodiments may take the form of a linear bar, a cube or other structure. In particular embodiments, bead 240 is a portion of the end of cable 212 deformed (e.g. heat-formed or molded) into a laterally-enlarged shape, and in other embodiments bead 240 is an item or substance molded, crimped, glued or otherwise attached to cable 212. The lateral dimension of bead 240 is small enough to fit between parts of a filter (e.g. through one portion of a gap 26 between wires 22 in filter 20) but larger than the breadth between parts at another point (e.g. at pinch-point 28 of that particular gap 26). As an example, a lateral dimension of a bead, ball, or knot 240 can be about 1 to 2 millimeters, and in a particular embodiment about 1.14 millimeters. In particular embodiments, bead 240 is of a substance that is visually observable under ultrasound, magnetic resonance imaging, CT scanning, x-ray or other visualization methods. As one example, bead 240 may be of a material visualizable under ultrasound, but having different sound reflection qualities than the rest of cable 212, so as to be able to clearly differentiate bead 240 from cable 212 under ultrasound visualization.

In the illustrated embodiment, cable 212 includes (and/or extends into or through part or all of) an inner sleeve, tube or grip 244, and sleeve 244 extends through part or all of lumen 228 of sheath 210. As previously noted, cable 212 and sheath 210 are movable longitudinally with respect to each other, so that bead 240 can be within tip 222 and/or lumen 228 of sheath 210 at a most-proximal relative position (e.g. within sheath 210 to a distance permitting the entirety of a filter to enter sheath 210, as in FIG. 9). Similarly, bead 240 can extend from tip 222 at a most-distal relative position (e.g. one-quarter or more of the length of a filter to be retrieved or removed, as in FIG. 8). A mechanism controlling cable 212 from outside the patient (not shown) may include handles, linkages and other suitable components (including mechanized components) for imparting forward and/or backward relative longitudinal movement of cable 212 and/or sheath 210. As seen in the embodiment of FIG. 8, cable 212 is extendable to a length several times the diameter of tip 222 beyond tip portion 222.

Use of system 200 will now be described in conjunction with an embodiment of filter 20 within a blood vessel V (FIGS. 7-9). It will be understood that use in conjunction with other filters or in other bodily environments is also contemplated.

With filter 20 inserted into vessel V, blood can flow through gaps 26 in filter 20, while passage of emboli or other solid matter of a particular size is limited or inhibited by wires 22.

Eventually, embolitic material collected by filter 20 can dissolve back into the bloodstream, or such material can be removed with filter 20.

At such time as the physician determines that filter 20 is no longer needed, or for another reason decides filter 20 should be moved or removed, access to the vessel and filter 20 is re-established (if access has not been maintained throughout the time that filter 20 has been in the patient). In particular embodiments, a cannula, sheath or other entry device (not shown) is placed in the same or similar location in the patient to allow access along the same or similar path through the vasculature. Sheath 210 is inserted into the patient via that access and maneuvered into vessel V so that tip portion 222 is adjacent or in close proximity to collar 24 of filter 20. From tip 222 of sheath 210, cable 212 with bead 240 is extended so that bead 240 moves through one of gaps 26 between wires 22 of filter 20. In one example, cable 212 is extended along a "top" portion of filter 20 so that as bead 240 moves forward gravity can assist in moving bead down through a gap 26. Sheath 210 may be adjusted longitudinally, laterally, and/or rotationally with respect to the filter as may be indicated or needed to place bead 240 through a pair of wires 22 and into the gap 26 between them. However, bead 240 can be inserted through any of gaps 26, and so the physician or other professional need not be so exact or precise as is generally necessary in connecting with or gripping an extraction hook.

With bead 240 and perhaps a portion of cable 212 within a gap 26 (e.g. FIG. 8 or 9), cable 212 is retracted until bead 240 becomes captured or engages wires 22 on either side of gap 26, e.g. when bead 240 approaches or is at pinch-point 28 of the gap 26, or is otherwise at a position at which gap 26 is smaller than the lateral dimension of bead 240. In a particular embodiment, cable 212 is retracted until bead 240 affirmatively engages filter 20 such that tension is created in cable 212, i.e., further pulling of cable 212 will transfer pulling force to filter 20. A slight tug on cable 212 with bead 240 engaged to the filter helps to straighten the filter up (if necessary) for introduction into sheath 210. This approach can also be very helpful where the top portion of the filter may be embedded into the vessel wall. With the filter tethered by bead 240 and cable 212, pulling cable 212 can better align filter 20 with sheath 210 and/or move filter 20 toward sheath 210, and maintaining tension on cable 212 (holding the filter in place) allows movement of sheath 210 toward the filter.

Once the user has engaged bead 240 with wires 22 of filter 20, tension can be maintained on cable 212, and the user moves sheath 210 toward filter 20 while maintaining tension on cable 212 (represented by arrow S, FIG. 8). Such a use may be indicated or appropriate in embodiments in which significant cellular growth to or around wire(s) 22 of filter 20 has occurred. As sheath 210 approaches filter 20, the opening of tip 222 approaches collar 24. Edge 238 and outer surface(s) 230 of tip portion 222 move between filter 20 and the wall of vessel V, e.g. through cells or tissue on or around filter 20. In this way, such cells or tissue can be parted, with cells or tissue adjacent to the wall of vessel V generally pushed toward the vessel wall, and cells or tissue adjacent wires 22 of filter 20 being pushed generally toward filter 20. In embodiments in which edge 238 is relatively sharp, it may slice through the cells or tissue between the vessel wall and the filter. To assist in its movement between the vessel and filter, tip 222 (with the rest of sheath 210 if fixed to it) can be rotated during or in conjunction with longitudinal movement to assist in freeing the filter from such cells or tissue. Flat surfaces 230 minimize surface area facing the vessel wall, minimizing potential injury.

Sheath 210 is moved over filter 20 while tension is maintained on cable 212, so that at least a portion of filter 20 is within sheath 210. In an embodiment as in FIG. 9, sheath 210 is moved sufficiently so that the entirety of filter 20 is within sheath 210 (i.e. within lumen 228). When filter 20 is within sheath 210 entirely or to a desired degree, sheath 210 is withdrawn from the patient. This allows the tip of the sheath to be gradually advanced toward an embedded filter or part of a filter. Rotation of tip 222 as needed, freeing the embedded portion of the filter 20, can be performed and, without losing capture or swapping out devices, filter 20 can now be removed. A new filter (or another type of device, such as a stent) may be placed at the same or a similar location after the removal of filter 20, if desired.

Alternatively or additionally, when cable 212 is in tension with filter 20 the user may continue pulling cable 212 to move filter 20 through vessel V toward tip portion 222 of sheath 210 (represented by arrow R, FIG. 8). Such a use may be indicated or appropriate in embodiments in which filter 20 is not embedded in or significantly attached to endothelial cells or tissue of the vessel. As cable 212 is further retracted, filter 20 enters tip 222 and is pulled into lumen 228. Inner surface 232 of tip 222 engages wires 22 to compress them radially (akin to folding an umbrella) as the wires move into lumen 228. In particular embodiments, filter 20 is drawn wholly into sheath 210 (e.g. FIG. 9) so that no part of filter 20 remains beyond tip 222, to minimize risk of damage during withdrawal of sheath 210 from the patient. When cable 212 has been retracted sufficiently, sheath 210 is withdrawn from the patient. A new filter (or another type of device, such as a stent) may be placed at the same or a similar location after the removal of filter 20, if desired.

In the discussion above, blood vessels have been used as the principal example of a location for placement of embodiments of filter 20. It will be understood that embodiments of filter 20 can be used in other vessels, organs or body parts where it is desired to allow flow of fluid yet contain solid or semi-solid materials from traveling through such parts unchecked.

Figure 6:
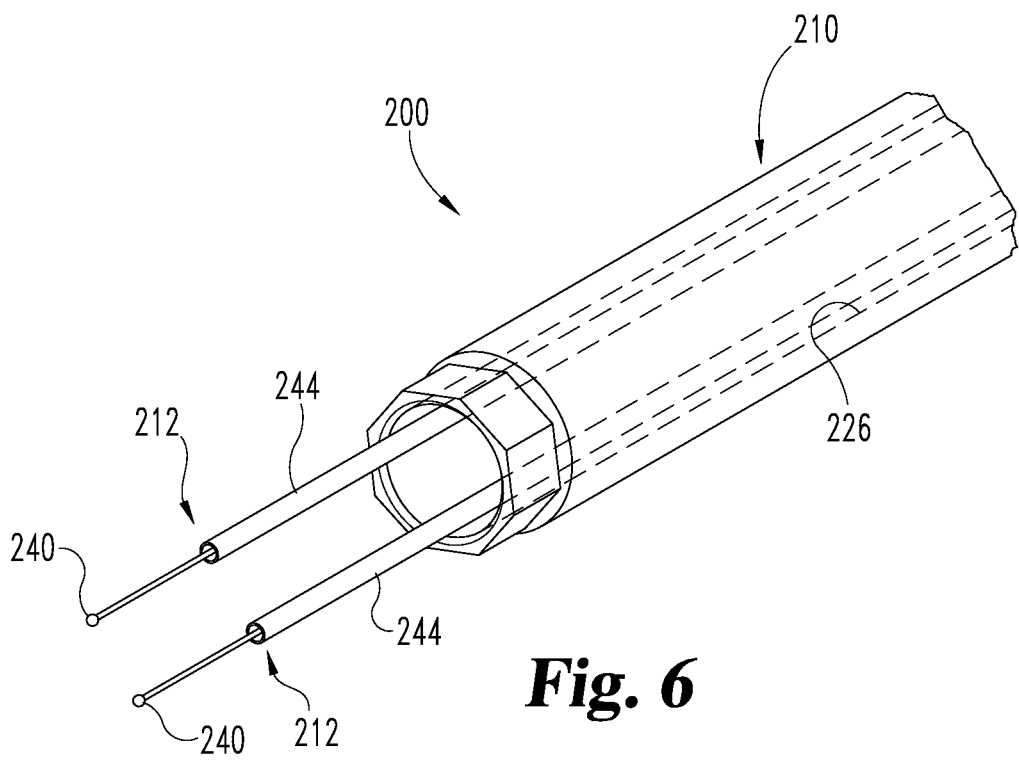
FIG. 6 is a perspective view of an embodiment of an internal filter retrieval system.

In other embodiments of system or device 200, multiple cables 212 are provided in connection with a single sheath 210 (e.g. FIG. 6). In the embodiment illustrated in FIG. 6, cables 212 and sheath 210 are substantially as described above. Two such cables 212 are shown, diametrically opposed to each other across the width of sheath 210. In other embodiments, cables 212 may be spaced less than 180 degrees from each other along the circumference of sheath 210, and/or one or both cables 212 may be placed inward of the edge of sheath 210. It will be understood that three, four or more cables 212 may be a part of device or system 210 in similar embodiments, equally-spaced from each other or in other relative orientations or placements.

Each cable 212 has at least one respective bead, knot, ball or similar protrusion 240, e.g. as in embodiments described above. Each may also include or extend into or through all or part of a respective sleeve, tube or grip 244 through all or part of lumen 228 in sheath 210. As noted above, one or more mechanisms to control cable(s) 212 from outside the patient, e.g. for imparting forward and/or backward relative longitudinal movement of cable(s) 212 and/or sheath 210, may be provided. In particular embodiments, such mechanism(s) permit each cable 212 to be operated or moved independently of the other(s). As will be described further below, such independent operability allows the user to choose which cable(s) 212 to use, and to operate cable(s) 212 in succession to vary force applied to a filter 20. In other embodiments, two or more cables 212 may be simultaneously operable by one mechanism, for substantially equal application of such cable(s) 212 to a filter 20.

Use of a device or system 200 with multiple cables 212 is essentially as described previously. To summarize, extension of one or more cables 212 so that associated bead(s) 240 move between and through wires 22 of a filter 20, allowing engagement of the beads 240 in a pinch-point 28 of between two or more wires 22. Retraction of cable(s) 212 provide tension to brace filter 20 or pull on filter 20, so that filter 20 can be placed within sheath 210, as by advancing sheath 210 over cable(s) 212 and filter 20 and/or pulling filter 20 into sheath 210.

In embodiments in which multiple cables 212 are independently operable, the user may extend at least first and second such cables 212 so that they are between wires and their respective beads 240 are within filter 20. Cables 212 may be independently retracted to engage different pinch-points 28. Pulling further on a first cable 212 exerts a force on one portion of filter 20, so as to better align or otherwise move or dislodge an adjacent portion of filter 20. Applying pulling force via a second cable 212 to a second portion of filter 20 (e.g. a diametrically-opposed portion) further adjusts alignment or otherwise moves or dislodges that second portion of filter 20, particularly in conjunction with a release or reduction of tension or force applied through the first cable 212. Where cables 212 are not independently movable and/or the user chooses not to use cables 212 to pull filter 20 toward sheath 210, the cables 212 and their respective beads, knots or protrusions 240 can be each used as braces (as described above). Sheath 210 can be moved forward over cables 212, with cables 212 in tension and their beads 240 as backstops, so that sheath 210 moves over filter 20. In cases in which pulling filter 20 is possible or desirable, by alternating pulling force between or among multiple independently-movable cables 212 linked to different parts of a filter 20, the filter can be alternately pulled on different sides or "walked" along or out of a vessel, e.g. into sheath 210.

Embodiments with multiple cables 212 with their respective beads 240 allow the user greater freedom regarding initial positioning of device 200, as in any initial position the user can use at least the most convenient or best-positioned cable 212. Further, using multiple cables 212 distributes force between or among cables 212 and between or among parts of filter 20, reducing the potential for bending wires of filter 20 or pulling a particular bead 240 through the filter. In cases in which epithelium or other matter has partially or completely covered at least a portion of the filter, embodiments with multiple cables 212 that are independently movable allow pulling force to be applied variably at different portions of the filter 20 to ease the filter 20 from the covering matter.

While the embodiments have been illustrated and described in detail in the drawings and foregoing description, the same is to be considered as illustrative and not restrictive in character, it being understood that only particular embodiments have been shown and described and that all changes and modifications that come within the spirit of the disclosure are desired to be protected. It will be understood that features or attributes noted with respect to one or more specific embodiments may be used or incorporated into other embodiments of the structures and methods disclosed. Further, the term "system" used above is intended to indicate both a situation in which sheath 210 and cable 212 are a single device, and one in which they are separate devices used together.

What is claimed is:

1. A retriever for an intravascular filter having a plurality of wire portions each separated by at least one gap, the retriever comprising:
a sheath having a generally cylindrical body through which a lumen extends, a distal end portion, and at least two elongated members at least partially within the lumen, the distal end portion having a plurality of flat outer surfaces in a generally polygonal shape and a sharpened leading edge tapering inwardly, the elongated members and sheath being movable longitudinally with respect to each other and with respect to the sheath, wherein each said elongated member includes a respective distal end and a respective protrusion at or adjacent the distal end for interlocking with and applying force to the filter as the filter enters the lumen.

2. The retriever of claim 1, wherein the plurality of substantially flat surfaces are substantially parallel to a longitudinal axis of the sheath.

3. The retriever of claim 1, wherein the inner surface borders a portion of the lumen and narrows as it extends away from the edge.

4. The retriever of claim 1, wherein the edge is a circular sharp edge and said sharp edge is adapted to cut through cells or tissue around the filter.

5. The retriever of claim 1, wherein the elongated member is a cable.

6. The retriever of claim 1, wherein the protrusion is a substantially spherical bead, having a diameter smaller than a largest width of one of the gaps and larger than a smallest width of the one of the gaps.

7. The retriever of claim 1, wherein the protrusion is smaller than a first portion of the gap and larger than a second portion of the gap so that the protrusion can be caught inside the filter between at least two of the wire portions.

8. The retriever of claim 1, wherein relative movement of the elongated member and the sheath resulting in the protrusion being within the lumen is adapted to place the filter within the lumen through the tip portion.

9. The retriever of claim 1, wherein a first and second of said elongated members are spaced diametrically apart across the width of the sheath.

10. The retriever of claim 1, wherein a first and second of said elongated members are spaced apart less than 180 degrees.

11. The retriever of claim 1, wherein the sheath has a distal internal space to accommodate the filter, wherein the entirety of the filter is positionable within the distal internal space.

12. A retrieval system for retrieving an emplaced internal medical filter comprising:
a retrieval sheath having a generally cylindrical body portion that includes a lumen at least in a distal portion, said sheath having a distal tip portion with a central opening communicating with the lumen, a plurality of flat outer surfaces around the central opening in a generally polygonal shape and at least one sharpened edge tapering inwardly; and
at least first and second cables extending at least partially through the retrieval sheath, the cables each having a respective distal end and a protrusion at or adjacent the distal end, the cables being movable longitudinally with respect to each other and with respect to the retrieval sheath between a first relative position in which the respective protrusions extend beyond the tip portion of the retrieval sheath by at least one-quarter of a length of the filter and a second relative position in which the respective protrusions are within the retrieval sheath, wherein the cables have a respective length dimension and the respective protrusions have a lateral dimension substantially perpendicular to the respective length dimension that is wider than at least a portion of a gap in the filter, and wherein the respective protrusions are adapted for interlocking with the filter and applying force to the filter as it enters the lumen.

13. The retrieval system of claim 12, wherein the edge is a circular sharp edge and said sharp edge is adapted to cut through cells or tissue around the filter.

14. The retrieval system of claim 12, wherein the retrieval sheath has a longitudinal axis and the tip portion is centered on the axis.

15. The retrieval system of claim 14, wherein the plurality of substantially flat surfaces are substantially parallel to the axis.

16. The retrieval system of claim 14, wherein the outer surface consists essentially of a plurality of substantially flat surfaces that are substantially parallel to the axis.

17. The retrieval system of claim 14, wherein the protrusion is one of (a) substantially spherical and (b) substantially linear and non-parallel to a longitudinal axis of the elongated member.

18. The retrieval system of claim 12, wherein a first and second of said elongated members are spaced diametrically apart across the width of the sheath.

19. The retrieval system of claim 12, wherein a first and second of said elongated members are spaced apart less than 180 degrees.

20. The retrieval system of claim 12, wherein the sheath has a distal internal space to accommodate the filter, wherein the entirety of the filter is positionable within the distal internal space.

* * * * *